United States Patent
Lawson et al.

(10) Patent No.: US 6,469,131 B2
(45) Date of Patent: *Oct. 22, 2002

(54) STRUCTURED COMPOSITION CONTAINING TERTIARY AMIDE-TERMINATED POLYAMIDE FOR PERSONAL CARE PRODUCTS

(75) Inventors: Nelson E. Lawson; Mark S. Pavlin, both of Savannah, GA (US)

(73) Assignee: Arizona Chemical Company, Jacksonville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/899,812

(22) Filed: Jul. 6, 2001

(65) Prior Publication Data

US 2002/0035237 A1 Mar. 21, 2002

Related U.S. Application Data

(63) Continuation-in-part of application No. 09/225,889, filed on Jan. 4, 1999, now Pat. No. 6,268,466.

(51) Int. Cl.$^7$ .......................... C08G 69/02; C08G 69/26
(52) U.S. Cl. .................. 528/335; 424/70.1; 424/70.11; 424/70.122; 424/70.17; 424/70.21; 528/332; 528/339; 528/339.3
(58) Field of Search ................................ 528/352, 335, 528/339.3, 339; 424/70.1, 70.11, 70.122, 70.17

(56) References Cited

U.S. PATENT DOCUMENTS

| | | | |
|---|---|---|---|
| 2,379,413 A | * 7/1945 | Bradley | |
| 2,450,940 A | * 10/1948 | Cowen et al. | |
| 2,662,068 A | * 12/1953 | Floyd | |
| 2,861,048 A | * 11/1958 | Wright et al. | |
| 3,141,787 A | * 7/1964 | Goetze et al. | 106/252 |
| 3,148,125 A | * 9/1964 | Strianse et al. | 167/85 |
| 3,156,572 A | * 11/1964 | Carlick et al. | 106/27 |
| 3,341,465 A | * 9/1967 | Kaufman et al. | 252/316 |
| 3,420,789 A | 1/1969 | Wilson | |
| 3,595,816 A | 7/1971 | Barrett | |
| 3,615,289 A | 10/1971 | Felton | 44/7.5 |
| 3,645,705 A | 2/1972 | Miller et al. | 44/7.5 |
| 3,819,342 A | 6/1974 | Gunderman et al. | 44/7.5 |
| 4,051,159 A | 9/1977 | Tsoucalas et al. | |
| 4,062,819 A | 12/1977 | Mains et al. | |
| 4,128,436 A | 12/1978 | O'Hara et al. | 106/243 |
| 4,150,002 A | 4/1979 | Drawert et al. | |
| 4,259,183 A | 3/1981 | Cadotte | 210/654 |
| 4,275,054 A | 6/1981 | Sebag et al. | 424/65 |
| 4,337,298 A | 6/1982 | Karim et al. | 428/461 |
| 4,341,671 A | 7/1982 | Bolze et al. | 528/324 |
| 4,376,194 A | 3/1983 | Tanaka et al. | 528/288 |
| 4,438,240 A | 3/1984 | Tannaka et al. | 525/420 |
| 4,552,693 A | 11/1985 | Hussain et al. | 252/522 A |
| 4,571,267 A | 2/1986 | Drawert et al. | 106/27 |
| 4,663,428 A | 5/1987 | Okitu et al. | 528/324 |

(List continued on next page.)

FOREIGN PATENT DOCUMENTS

| | | | |
|---|---|---|---|
| EP | 467 533 A1 | * | 1/1992 |
| EP | 469 435 A1 | * | 2/1992 |
| EP | 1 068 855 A1 | * | 1/2001 |
| EP | 1 068 856 A1 | * | 1/2001 |
| WO | WO 98/17243 | * | 4/1998 |
| WO | WO 98/17705 | * | 4/1998 |

OTHER PUBLICATIONS

Tóth et al., "Analytical Performances of Lipophilic Diamides Based Alkaline Earth Ion–Selective Electrodes," *Electroanalysis* 5(9–10):781–790, 1993.*

Vedanayagam et al., "Kinetics of Reaction of $C_{36}$ Dimeric Fatty Acids and Ethylenediamine in Solution," *J. Applied Polymer Science* 45(12):2245–2248, 1992.*

Yasuda et al., "Novel Low–molecular–weight Organic Gels:N, N', N"—Tristearyl trimesamide/Organic Solvent System," *Chemistry Letters* :575–576, 1996.*

*Primary Examiner*—Fred Zitomer
(74) *Attorney, Agent, or Firm*—Seed Intellectual Property Law Group PLLC

(57) ABSTRACT

1. A structured composition comprising at least one liquid oil phase structured by at least one gellant, said at least one gellant comprising a tertiary amide-terminated polyamide resin (ATPA) of the formula (1):

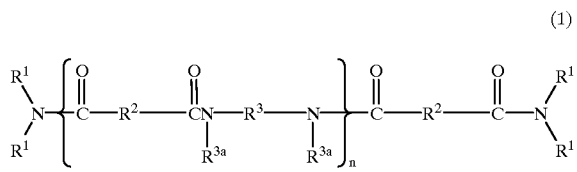

(1)

wherein, n designates a number of repeating units such that terminal amide groups constitute from 10% to 50% of the total amide groups; $R^1$ at each occurrence is independently selected from a $C_{1-22}$ hydrocarbon group; $R^2$ at each occurrence is independently selected from a $C_{2-42}$ hydrocarbon group; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$; the composition further comprising at least one amphiphile compound that is a liquid at ambient temperature or has a melting point below 35° C., and has an HLB value of less than 8.0.

33 Claims, No Drawings

U.S. PATENT DOCUMENTS

| | | | |
|---|---|---|---|
| 4,742,128 A | 5/1988 | Frisch et al. | 525/424 |
| 4,742,147 A | 5/1988 | Nichols | 528/75 |
| 4,760,117 A | 7/1988 | Evans et al. | 525/394 |
| 4,769,285 A | 9/1988 | Tasmussen | 428/355 |
| 4,816,549 A | 3/1989 | Rumack | 528/336 |
| 4,937,069 A | 6/1990 | Shin | 424/66 |
| 4,946,922 A | 8/1990 | Reisch et al. | 528/76 |
| 5,069,897 A | 12/1991 | Orr | 424/66 |
| 5,102,656 A | 4/1992 | Kasat | 424/66 |
| 5,177,177 A | 1/1993 | Thullen et al. | 528/339.3 |
| 5,342,894 A | 8/1994 | Robeson et al. | 525/183 |
| 5,364,924 A | 11/1994 | Gerkin et al. | 528/73 |
| 5,372,852 A | 12/1994 | Titterington et al. | 427/288 |
| 5,432,204 A | 7/1995 | Farkas | 521/49 |
| 5,500,209 A | 3/1996 | Ross et al. | 424/66 |
| 5,538,718 A | 7/1996 | Aul et al. | 424/64 |
| 5,603,925 A | 2/1997 | Ross et al. | 424/65 |
| 5,645,632 A | 7/1997 | Pavlin | 106/31.29 |
| 5,783,657 A | 7/1998 | Pavlin et al. | 528/310 |
| 6,268,466 B1 | 7/2001 | MacQueen et al. | 528/335 |

\* cited by examiner

STRUCTURED COMPOSITION CONTAINING TERTIARY AMIDE-TERMINATED POLYAMIDE FOR PERSONAL CARE PRODUCTS

CROSS-REFERENCE TO RELATED APPLICATION

This application is a continuation-in-part of U.S. patent application Ser. No. 09/225,889, filed Jan. 4, 1999, now U.S. Pat. No. 6,268,466, which application is incorporated herein by reference in its entirety.

TECHNICAL FIELD

The present invention is directed to a composition for the care and/or treatment and/or makeup of the skin, including the scalp and/or lips of human beings. The composition contains a liquid oil phase gelled with a particular gellant and may be supplied as a self-supporting stick, for example, a lipstick, and whose application leaves a glossy deposit that does not bleed or wick.

BACKGROUND OF THE INVENTION

Cosmetic or dermatological products often contain a liquid oil phase that is structured, i.e., either thickened, gelled or rendered rigid; in particular, this is the case for solid compositions such as deodorants, salves and lipstick, products for rings under the eyes and cast makeup foundation. This structuring is typically obtained by incorporating waxes and/or fillers into the formulation. Unfortunately, these waxes and fillers tend to render the composition matte, and that is not always desirable, especially for lipstick. Women prefer a lipstick in the form of a rod that leaves a highly glossy film.

Structuring the liquid oil phase limits the exudation or bleeding of the solid compositions and also limits, after application on the skin or lips, the migration of this phase into wrinkles and lines, also called wicking. Migration is particularly undesireable for a lipstick. The considerable migration of the liquid oil phase containing colorants causes an unpleasant esthetic appearance around the lips, particularly accentuating wrinkles and lines. This migration is often mentioned by women as a major fault with conventional lipstick.

Gloss or or shininess is related primarily to the nature of the liquid oil phase. It is possible to reduce the quantity of waxes and fillers in the composition in order to increase the shine of a lipstick, but the tendency toward migration of the liquid oil phase then increases. In other words, the levels of waxes and fillers typically required to manufacture a lipstick without a tendecy toward wicking reduce the shininess of the deposited film.

The present invention is directed to a composition for care products and/or makeup and/or skin treatment and or lips that can remedy these disadvantages.

SUMMARY OF THE INVENTION

In one aspect, the present invention provides a structured composition that includes at least one liquid oil phase structured by at least one gellant. The at least one gellant includes a tertiary amide-terminated polyamide resin (ATPA) of the formula (1):

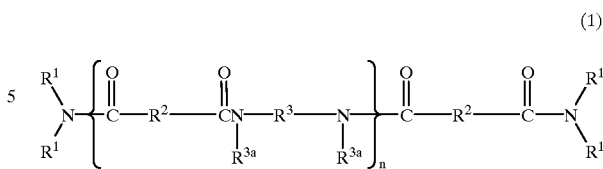

(1)

wherein, n designates a number of repeating units such that terminal amide groups constitute from 10% to 50% of the total amide groups; $R^1$ at each occurrence is independently selected from a $C_{1-22}$ hydrocarbon group; $R^2$ at each occurrence is independently selected from a $C_{2-42}$ hydrocarbon group; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$; wherein the composition further includes at least one amphiphile compound that is a liquid at ambient temperature or has a melting point below 35° C., and has an HLB value of less than 8.0. In one aspect of the invention, the amphiphile is a liquid at ambient temperature.

In another aspect, the present invention provides a structured composition that includes a cosmetically acceptable medium containing at least one liquid-fatty phase structured by at least one gellant. The at least one gellant includes a tertiary amide-terminated polyamide resin (ATPA) of the formula (1):

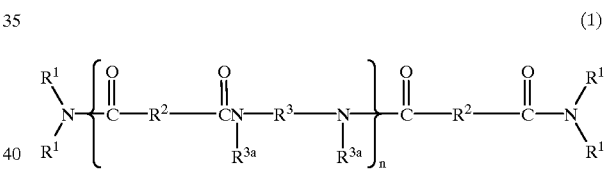

(1)

wherein, n designates a number of repeating units such that terminal amide groups constitute from 10% to 50% of the total amide groups; $R^1$ at each occurrence is independently selected from a $C_{1-22}$ hydrocarbon group; $R^2$ at each occurrence is independently selected from a $C_{2-42}$ hydrocarbon group; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$; wherein the composition further includes at least one amphiphile compound that is liquid at ambient temperature or has a melting point below 35° C., and has an HLB value of less than 8.0. In one aspect of the invention, the amphiphile is a liquid at ambient temperature.

In characterizing the compositions of the present invention, one or more of the following criterion may be independently selected and included in the description of the invention, so long as the criterion are non inconsistent with one another: The terminal amide groups of the formula $C(=O)N(R^1)(R^1)$ constitute from 20% to 35% of the total of the amide groups. The integer n is from 1 to 5. $R^2$ is a $C_{30-42}$ hydrocarbon group having the structure of polymerized fatty acid with the carboxylic acid groups removed. Between 1% and 50% of the $R^2$ groups are a $C_{4-19}$ hydrocarbon group. $R^3$ is a $C_{2-36}$ hydrocarbon group and $R^{3a}$ is hydrogen. At least 1% of the —$N(R^{3a})$—$R^3$—$N(R^{3a})$— groups are independently selected from polyalkylene amine,

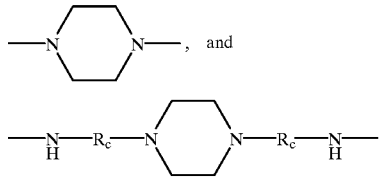

wherein $R_c$ is a $C_{1-3}$ alkyl group. The composition includes diamide having formula (1) wherein n=0, such that the ratio of terminal amide groups to the total of the amide groups in the resin is from 0.1 to 0.7.

The amphiphile compound includes a lipophile part covalently bonded to a polar part, with the lipophile part including a carbon chain having at least 8 carbon atoms. The amphiphile compound includes a lipophile part bonded to a polar part, with the lipophile part including a carbon chain having at least 16 to 32 carbons. The amphiphile compound includes a lipophile part covalently bonded to a polar part, with the lipophile part including a carbon chain having at least 18 to 28 carbons. The polar part of the amphiphile compound is selected from the group of alcohols and polyols having from 1 to 12 hydroxyl groups, polyoxyalkylenes having at least 2 oxyalkylene groups and having from 0 to 20 propoxylated groups and/or from 0 to 20 ethoxylated groups. The amphiphile compound is selected from:

(a) an ester of stearic, palmitic, behenic, hydroxystearic, oleic, or isostearic acid or mixtures thereof and glycerol, ethylene glycol, propylene glycol, sucrose, sorbitol, or methylglucose;

(b) an polyoxyalkene ether of a C-12 to C-26 branched- or linear-chain fatty alcohol such as stearyl alcohol or castor oil and;

c) a C-12 to C-26 branched-chain fatty alcohol such as octyldodecanol, and their mixtures.

The amphiphile compound is from 2% to 15% of the total weight of the composition. The ATPA resin is from 5 to 40% of the total weight of the composition. The fatty phase includes more than 50% oil or a mixture of non-polar oils. The oil phase includes at least one hydrocarbon oil of mineral or synthetic origin. The liquid oil phase includes at least one oil selected from parleam oil, isoparaffins, and squalane or mixtures thereof. The liquid oil phase is from 5 to 99% of the total weight of the composition. The liquid oil phase is from 20 to 75% of the total weight of the composition. The composition is formulated for the care and/or treatment and/or making-up of keratinous substances. The composition further includes at least one coloring agent. The composition includes at least one coloring agent, where the coloring agent is chosen from lipophile coloring agents, hydrophile coloring agents, pigments, mother-of-pearl, and mixtures thereof. The composition includes coloring agent where the coloring agent is from 0.01 to 40% of the total weight of the composition. The composition further includes at least one additive selected from water, antioxidants, essential oils, preservatives, neutralizers, liposoluble polymers, cosmetic or dermatological active principles, fillers, perfumes, waxes, and mixtures thereof. The composition is in a molded form, i.e., it has been cast into and then taken from a mold. The composition is in the form of, i.e., has been formulated to function as a mascara, eye liner, make-up foundation, lipstick, deodorant, insect repellent, body make-up, make-up remover, eye shadow, rouge, product to remove rings round the eyes, medicated shampoo or creme rinse, sun protection product, or face or body care product. The composition has a hardness of between 20 and 2,000 g at ambient temperature.

The invention also provides a cosmetic care, make-up or treatment process for the keratinous substances of human beings that includes the application on the keratinous substances of any of the compositions as summarized above.

In another aspect, the invention provides a process for the treatment or care of keratinous substances of a human being, comprising the application onto the keratinous substance of any of the compositions summarized above.

In another aspect, the present invention provides a method for forming a structured composition as described above, where the method includes combining ATPA at elevated temperature with at least one liquid oil phase and at least one amphiphile compound that is a liquid at ambient temperature or has a melting point below 35° C., and has an HLB value of less than 8.0, so as to form a homogenous solution upon stirring, and allowing the homogenous solution to cool to ambient temperature. In one aspect, the amphiphile is a liquid at ambient temperature.

The forgoing summary presents some noteworthy aspects of the present invention, where these and additional aspects and features of the present invention are described in more detail below.

DETAILED DESCRIPTION OF THE INVENTION

The present invention relies on the surprising discovery that the use of a particular gellant enables liquid oil phases to be structured, even in the absences of wax, in the form of a stick whose application on the lips leads to a glossy and non-migrating film. More precisely, the aim of the present invention is a structured composition containing at least one liquid oil phase structured with at least one gellant referred to herein as ATPA., where this structured composition is formulated as a personal care product In one aspect, this gellant is combined with at least one other material, where the second material is an amphiphile having an HLB value lower than 8.0.

By liquid oil phase in the sense of the present invention, is meant an oil phase that is liquid at room temperature (25° C.) and atmospheric pressure (760 mm Hg) composed of one or several mutually compatible lipophilic materials, also called oils. By definition, an oil will have an HLB value of less than 1.0. HLB is the hydrophilic/lipophilic balance. If a material has an HLB value of less than 1.0, it will dissolve readily in a liquid n-alkane such as n-decane and, if shaken in intimate contact with water, essentially will not partition into the water phase.

According to the invention, one may use one or several amphiphilic substances, preferably that are liquid at room temperature (25° C.) and at atmospheric pressure. This amphiphilic compound or mixture of amphiphilic compounds preferably has an HLB value in the range of 1.0 to 7.0, even better from 1.0 to 5.0 and still better from 3.0 to 5.0. The purpose of the amphiphile is to reinforce the structuring properties of the ATPA gellant, increase formulation clarity, facilitate use and improve stick application capacity.

The ATPA gellants of the composition of the invention present good solubility in oils as a result of their alkyl or alkenyl chain at the extremity of the polyamide skeleton and thus lead to macroscopically homogeneous compositions, even with a high concentration (at least 25%) of gellant.

The gellant according to the present invention is a resin comprising short-chain polyamides of the formula (1), which will be referred to herein as tertiary amide-terminated polyamides, or ATPAs.

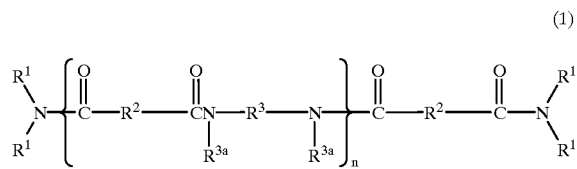

(1)

In formula (1), n designates a number of repeating units such that terminal (i.e., $R^1$-containing) amide groups constitute from 10% to 50% of the total of the amide groups shown in formula (1); $R^1$ at each occurrence is independently selected from a $C_{1-22}$ hydrocarbon group; $R^2$ at each occurrence is independently selected from a $C_{2-42}$ hydrocarbon group with the proviso that at least 50% of the $R^2$ groups have 30–42 carbon atoms; $R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$, such that at least 50% of the $R^{3a}$ groups are hydrogen.

Preferably, the gellant comprises diamide having formula (1) wherein n=0, such that the ratio of terminal amide groups to the sum of amide groups in the total of the molecules that comprise the resin of formula (1) is from 0.1 to 0.7. Preferably, the resin composition is at reaction equilibrium.

As may be seen from formula (1), the ATPA resins have terminal amide groups of the formula —C(=O)N($R^1$)($R^1$) at both ends of a series of amide groups. These terminal amide groups are formed from secondary amines (since $R^1$ is an organic group and is not hydrogen), and therefore the terminal amide groups in formula (1) are properly referred to as tertiary amide groups. Accordingly, the ATPA resins may be referred to as tertiary amide-terminated polyamides.

The letter "n" in formula (1) designates the number of repeating units present in a molecule of ATPA, and is an integer greater than 0. According to the invention, n may be 1, in which case the ATPA contains equal numbers of terminal amide and non-terminal amide groups, i.e., the terminal amide groups constitute 50% of the total of the amide groups in the ATPA molecule. The preferred ATPA resins are of relatively low molecular weight, so that n is preferably 1 to about 10, and more preferably is 1 to about 5. Because the ATPA molecules have such a low molecular weight, they could equally well be referred to as tertiary amide-terminated oligoamides. In any event, viewed another way, the terminal amide groups constitute about 10% to about 50%, preferably about 15% to about 40%, and more preferably about 20% to about 35% of the total of the amide groups. A preferred ATPA resin includes a mixture of ATPA molecules of formula (1) having various n values. The ATPA resin has a weight average molecular weight of less than about 10,000, and typically less than about 5,000, but more than 500, typically more than 1,000, when measured by gel permeation chromatography using polystyrene calibration standards.

The $R^1$ group in formula (1) is a hydrocarbon group, and preferably is an alkyl or alkenyl group which contains at least 1, typically at least 4, and preferably more than 4 carbon atoms, e.g., 8, 10, 12, 14, 16, 18, 20, or 22 carbon atoms. Alkyl groups are preferred, however alkenyl groups having 1–3, and preferably 1 site of unsaturation are also suitable. The upper range for the number of carbon atoms in the $R^1$ group is not particularly critical, however preferably the $R^1$ group has less than or equal to about 22 carbon atoms. $R^1$ groups having about 16–22 carbon atoms are highly preferred. The identity of $R^1$ at any occurrence is independent of the identity of $R^1$ at any other occurrence.

Suitable $R^1$ groups are readily introduced into a molecule of formula (1) when secondary monoamine(s) is used as a co-reactant in preparing the ATPA resin. The secondary monoamine has the formula $HN(R^1)(R^1)$, wherein $R^1$ is defined above. Suitable secondary monoamines are commercially available from a variety of sources, including Witco Corporation (Greenwich, Conn.; http://www.witco.com); Akzo Nobel Chemicals, Surface Chemistry (Chicago, Ill.; http://www.akzonobelusa.com); and Aldrich (Milwaukee, Wis.; http://www.aldrich.sial.com). Di(hydrogenated tallow) amine is a preferred secondary monoamine.

The $R^2$ group in formula (1) is suitably a hydrocarbon containing 2 to 42 carbon atoms, and preferably contains 4 to 42 carbon atoms. A more preferred $R^2$ group contains 30–42 carbon atoms (i.e., is a $C_{30-42}$ group), and at least 50% of the $R^2$ groups in an ATPA resin preferably have 30–42 carbon atoms. Such $R^2$ groups are readily introduced into an ATPA when the resin is prepared from polymerized fatty acid, also known as dimer acid. Polymerized fatty acid is typically a mixture of structures, where individual dimer acids may be saturated, unsaturated, cyclic, acyclic, etc. Thus, a detailed characterization of the structure of the $R^2$ groups is not readily available. However, good discussions of fatty acid polymerization may be found in, for example, U.S. Pat. No. 3,157,681 and Naval Stores—Production, Chemistry and Utilization, D. F. Zinkel and J. Russel (eds.), Pulp. Chem. Assoc. Inc., 1989, Chapter 23. Dimer acid is available commercially as, for example, UNIDYME™ and SYLVADYM™ dimer acids from Arizona Chemical Corporation (Jacksonvill, Fla.), EMPOL™ dimer acid from Henkel Corporation, Emery Oleochemicals Division (Cincinnati, Ohio); PRIPOL™ dimer acid from Unichema North America (Chicago, Ill.).

While the preferred ATPA resins contain at least 50% $C_{30-42}$ groups as the $R^2$ group, more preferably the total of the $R^2$ groups consist of at least 75% $C_{30-42}$ groups, and still more preferably consist of at least 90% $C_{30-42}$ groups. ATPA resins of formula (1) wherein $R^2$ is entirely $C_{30-42}$ are preferred gelling agents of the invention.

However, ATPA resins may also contain $R^2$ groups having less than 30 carbon atoms. For example, an ATPA resin may contain one or more R groups having about 4 to 19, preferably about 4 to 12, and more preferably about 4 to 8 carbon atoms. The carbon atoms may be arranged in a linear, branched or cyclic fashion, and unsaturation may be present between any two carbon atoms. Thus, $R^2$ may be aliphatic or aromatic. When present, these lower carbon-number $R^2$ groups are preferably formed entirely of carbon and hydrogen, i.e., are hydrocarbyl groups. Such lower carbon-number $R^2$ groups preferably constitute less than 50% of the $R^2$ groups; however, when present, constitute about 1% to about 50%, and preferably about 5% to about 35% of the total of the $R^2$ groups. The identity of $R^2$ at each occurrence is independent of the identity of $R^2$ at any other occurrence.

Suitable co-diacids are available from, for example, Aldrich (Milwaukee, Wis.).

The —N($R^{3a}$)—$R^3$—N($R^{3a}$)— group in formula (1) links two carbonyl (C=O) groups. In a preferred embodiment of the invention, all of the $R^{3a}$ groups in an ATPA resin are hydrogen, so that $R^3$ alone joins the two nitrogen atoms shown in the formula —N($R^{3a}$)—$R^3$—N($R^{3a}$)—. In this case, the $R^3$ group contains at least two carbon atoms, and optionally oxygen and/or nitrogen atoms, in addition to any hydrogen atoms that are necessary to complete otherwise unfilled valencies of the carbon, oxygen and nitrogen atoms. In one embodiment, $R^3$ is a hydrocarbon group, having 2 to about 36 carbon atoms, preferably having 2 to about 12 carbon atoms, and more preferably having 2 to about 8 carbon atoms. These carbon atoms may be arranged in a linear, branched or cyclic fashion, and unsaturation may be present between any two of the carbon atoms. Thus, $R^3$ may contain aliphatic or aromatic structures. The identities of $R^3$ and $R^{3a}$ at each occurrence are independent of their identities at any other occurrence.

The $R^3$ groups may contain oxygen and/or nitrogen in addition to carbon and hydrogen atoms. A typical oxygen atom-containing $R^3$ group is a polyalkylene oxide, i.e., a group having alternating alkylene groups and oxygen atoms. Indeed, the oxygenation in a $R^3$ group is preferably present as an ether group. Representative polyalkylene oxides include, without limitation, polyethylene oxide, polypropylene oxide and copolymers (either random, alternating or block) of ethylene oxide and propylene oxide. Such oxygenated $R^3$ groups are readily introduced into an ATPA resin through use of JEFFAMINE™ diamines (Huntsman Chemical, Inc., Houston, Tex.). These materials are available in a wide range of molecular weights, where any molecular weight diamine may be used in the preparation of the resins of the invention. While some of the $R^3$ groups may contain oxygen (at least about 1%), preferably a minor number (less than 50%) of the $R^3$ groups contain oxygen, and more preferably less than about 20% of the $R^3$ groups contain oxygen. The presence of oxygen-containing $R^3$ groups tends to lower the softening point of the ATPA resin.

When present, the nitrogen atoms in an $R^3$ group are preferably present as secondary or tertiary amines. A typical nitrogen-containing $R^3$ group having secondary amine groups is a polyalkylene amine, i.e., a group containing alternating alkylene groups and amine groups, which is sometimes referred to as a polyalkylene polyamine. The alkylene group is preferably a lower alkylene group, e.g., methylene, ethylene, (i.e., —CH$_2$CH$_2$—), propylene, etc. A typical polyalkylene amine may be represented by the formula —NH—(CH$_2$CH$_2$NH)$_m$CH$_2$CH$_2$—NH— wherein m is an integer from 1 to about 5.

However, the nitrogen atoms in the nitrogen-containing $R^3$ group may alternatively (or additionally) be present as tertiary nitrogen atoms, e.g., they may be present in a heterocycle of the formula:

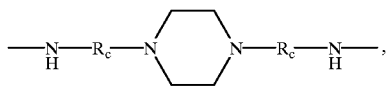

wherein $R_c$ is a $C_{1-3}$ alkylene group.

In the above-described nitrogen-containing $R^3$ groups, $R^{3a}$ was hydrogen. However, $R^{3a}$ is not limited to hydrogen. In fact, $R^{3a}$ may be a $C_{1-10}$alkyl group, preferably a $C_{1-5}$alkyl group, and more preferably a $C_{1-3}$alkyl group. In addition, $R^3$ and $R^{3a}$, or two $R^{3a}$ groups, may together form a heterocyclic structure, e.g., a piperazine structure such as

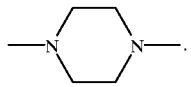

In this case, the two $R^{3a}$ groups may be seen as joining together to form an ethylene bridge between the two nitrogen atoms, while $R^3$ is also an ethylene bridge. Additional suitable diamines are available from, for example, Aldrich (Milwaukee, Wis.).

The ATPA resin typically includes a mixture of ATPA molecules of formula (1) in addition to, for example, by-products that are formed during the ATPA-forming reaction. While the ATPA molecules of formula (1) may be purified from such by-products using, for example, chromatography or distillation, the by-products are typically either minimal in amount or impart desirable properties to the resin when the resin functions as a gelling agent, and thus need not be separated from the molecules of formula (1) in order for a suitable ATPA resin to be formed.

As described herein, amines and carboxylic acids are preferred starting materials to form the ATPA resins of the invention. These starting materials are preferably reacted together with a stoichiometry, and under reaction conditions, such that the acid number of the resulting ATPA resin is less than 25, preferably less than 15, and more preferably less than 10, while the amine number is preferably less than 10, more preferably less than 5, and still more preferably less than 1. The softening point of the ATPA resin is preferably greater than room temperature, more preferably is about 50° C. to about 150° C., and still more preferably is about 80° C. to about 130° C.

It is important to control the stoichiometry of the reactants in order to prepare an ATPA resin according to the invention. In the following discussion regarding reactant stoichiometry, the terms "equivalent(s)" and "equivalent percent" will be used, and are intended to have their standard meanings as employed in the art. However, for additional clarity, it is noted that equivalents refer to the number of reactive groups present in a molar quantity of a molecule, such that a mole of a dicarboxylic acid (e.g., sebacic acid) has two equivalents of carboxylic acid, while a mole of monoamine has one equivalent of amine. Furthermore, it is emphasized that in preparing an ATPA resin, the diacid has only two reactive groups (both carboxylic acids), the monoamine has only one reactive group (a secondary amine group) and the diamine has only two reactive groups (preferably both primary amines), and these are preferably, although not necessarily, the only reactive materials present in the reaction mixture.

When co-diacid is employed to prepare an ATPA resin, the co-diacid preferably contributes no more than about 50% of the equivalents of carboxylic acid present in the reaction mixture. Stated another way, the co-diacid contributes from 0–50 equivalent percent of the acid equivalents in the reaction mixture. Preferably, the co-diacid contributes 0–30 equivalent percent, and more preferably contributes 0–10 equivalent percent of the acid equivalents in the reaction mixture.

The stoichiometry of the reactants will have a significant impact on the composition of the ATPA resin. For example, ATPA resins made with increasing amounts of secondary monoamine will tend to have lower (number and weight) average molecular weights. In other words, as more monofunctional reactant is used, the number of amide pairs in an average molecule of formula (1) will decrease. On the other hand, as less monoamine is used, the average molecular weight of the molecules in the ATPA resin will increase. In general, increasing the average molecular weight of the ATPA will tend to increase the melting point and melt viscosity of the resin. When a high melting point ATPA is combined with a solvent to thereby form a gel, the gel will tend to have a firmer consistency than does a gel formed from an ATPA with a low melting point.

In order to prepare an ATPA resin, the above-described reactants (diacid, monoamine and diamine, or reactive equivalents thereof) may be combined in any order. Preferably, the reactants are simply mixed together and heated for a time and at a temperature sufficient to achieve essentially complete reaction, to thereby form the ATPA resin. During formation of the ATPA resin, the diacid and diamine groups will alternate to form what may be termed an alternating copolymer. The ATPA is not a block copolymer. The terms "complete reaction" and "reaction equilibrium" as used herein have essentially the same meaning, which is that further heating of the product gelling agent does not result in any appreciable change in the acid or amine numbers of the resin.

Thus, the ATPA resin may be formed in a one-step procedure, wherein all of the diacid (including co-diacid), secondary monoamine, and diamine are combined and then heated to about 180–250° C. for a few hours, typically 2–8 hours. When lower temperatures are used, a longer reaction time is typically needed to achieve complete reaction. When the reaction temperature is too high, the reactants and/or products may undergo undesirable thermally-induced decomposition. Since one or more of the reactants may be a solid at room temperature, it may be convenient to combine each of the ingredients at a slightly elevated temperature, and then form a homogeneous mixture prior to heating the reaction mixture to a temperature sufficient to cause reaction between the diacid, monoamine and diamine. Alternatively, although less preferably, two of the reactants may be combined and reacted together, and then the third reactant is added followed by further heating until the desired product is obtained. Reaction progress may be conveniently monitored by periodically measuring the acid and/or amine number of the product mixture.

As one example, dimer acid may be reacted with diamine so as to form polyamide, and then this intermediate polyamide may be reacted with monoamine to form a tertiary amide-terminated dimer acid-based polyamide. Or, dimer acid may be reacted with the monoamine to thereby form diamide, and this diamide may be reacted with diamine to thereby form tertiary amide-terminated dimer acid-based polyamide. Because the components of the ATPA resin are preferably in reaction equilibrium (due to transamidation), the order in which the reactants are combined typically does not impact on the properties of the gelling agent.

Any catalyst that may accelerate amide formation between carboxylic acid and amine groups may be present in the reaction mixture described above. Thus, mineral acid such as phosphoric acid, or tin salts such as dibutyltin oxide, may be present during the reaction. In addition, it is preferred to remove water from the reaction mixture as it is formed upon amide formation. This is preferably accomplished by maintaining a vacuum on the reacting mixture, or by passing a gentle stream of an inert gas (e.g., nitrogen) across the top of the reaction mixture.

The composition of the invention may be a paste, solid or cream. It may be an oil-in-water and water-in-oil emulsion, a solid or soft anhydrous gel. It is preferably a translucent or transparent anhydrous gel, especially transparent anhydrous, cast in a stick, jar, pot or cup.

The amphiphilic components usable in the composition of the invention contain a lipophilic moiety covalently bound to a polar moiety, the lipophilic moiety containing a chain of at least 8 carbon atoms, in particular 16 to 32 carbon atoms, and better 18 to 28 carbon atoms. The polar moiety of this or these amphiphilic component(s) is preferably the rest of a compound chosen among alcohols and polyols having 1 to 12 hydroxyl groups, polyoxyalkylenes containing at least 2 oxyalkylene groups and having 0 to 20 polypropylene groups and/or 0 to 20 oxyethelene groups. In one aspect of the invention, the amphiphilic compound is chosen from:

(a) an ester of stearic, palmitic, behenic, hydroxystearic, oleic, or isostearic acid or mixtures thereof and glycerol, ethylene glycol, propylene glycol, sucrose, sorbitol, or methylglucose, and;

(b) a polyoxyalkene ether of a C-12 to C-26 branched- or linear-chain fatty alcohol alcohol such as stearyl alcohol or castor oil, and;

c) a C-12 to C-26 branched-chain fatty alcohol such as octyldodecanol; and their mixtures. Among the esters, monoesters and mixtures of mono- and di-esters are preferred.

The structuring or gelling of oils (in general of the liquid oil phase) that can be modulated by the nature of the ATPA gellant and by those of the amphiphilic compound used is such that a rigid structure can be obtained in the form of a rod or a stick.

The concentrations of the amphiphilic compounds and that of the ATPA gellant are chosen as a function of the desired degree of hardness of the gel and as a function of the particular planned application. The respective quantities of ATPA gellant and amphiphilic compound can be such that they enable a solid gel to be obtained that can disintegrate, does not flow under its own weight, and in one aspect has a hardness between 20 and 2000 g and better between 20 and 900 g, notably from 200 to 600 g and for example from 150 to 450 g. This hardness can be measured with the method of penetration of a probe in the said composition and in particular with a texture analyzer (for example Rhéo TA-XT2) equipped with an ebonite cylinder 5 mm high and 8 mm in diameter. Hardness is measured at 20° C. at the center of 5 samples of the said composition. The cylinder is introduced in each sample of the composition at a pre-speed of 2 mm/s then at a speed of 0.5 mm/s and finally at a post-speed of 2 mm/s, total displacement being 1 mm. The hardness value is that of the maximum peak. Measurement error is ±50 g.

Hardness can also be measured with the so-called "wire cutter" method, that involves cutting an 8.1 mm diameter rod of lipstick and measuring hardness at 20° C. with a DFGHS 2 dynamometer manufactured by Indelco-Chatillon, that moves at a speed of 100 mm/min. It is expressed as the shear force (expressed in grams) required to cut a stick in these conditions. Using this method, the hardness of a composition in stick according to the invention is between 30 and 160 g, preferably from 30 to 120 g, for example from 30 to 50 g.

This hardness is such that the composition is self-supporting and can disintegrate under a shearing force to form a satisfactory deposit on the skin and the lips. In addition, with this hardness the composition of the invention in a cast form, notably in sticks, is resistant to shocks. According to the invention, the composition in the form of a stick behaves as a deformable and supple elastic solid, conferring on the application a remarkable elastic softness.

In practice, the quantity of ATPA gellant typically represents (as active material) 0.5 to 80% of the total weight of the composition, preferably 5 to 40%. The quantity of amphiphilic compound represents in practice 0.1 to 35% and better 2 to 15%.

When these rods or sticks are colored, and in particular are pigmented, application of the rod onto skin furnishes a glossy, homogeneous colored deposit that does not migrate into the lines and wrinkles of the skin, in particular the lines and wrinkles surrounding the lips and the eyes.

Advantageously, the liquid oil phase structured by the gellant contains a major quantity, i.e., more than 40%, and better more than 50% by weight of oil or a mixture of non-polar liquid oils such as hydrocarbon compounds, with reference to the total weight of the liquid oil phase.

According to the invention, non-polar oils are in particular linear or branched hydrocarbons or fluorocarbons, either synthetic or mineral in origin, whether or not volatile, such as light paraffin oils (such as isoparaffins, isododecane), or non-volatile oils such as petrolatum, polydecenes, hydrogenated polyisobutene such as parleam, and squalane or squalene. The oils used are preferably non-polar hydrocarbon oils of mineral or synthetic origin, notably chosen among parleam oil, isoparaffins, squalane and their mixtures.

A preferred non-polar oil is a hydrocarbon oil, where the hydrocarbon may be aliphatic or aromatic. Mineral oils are a preferred non-polar oil, wherein in one embodiment, the mineral oil is food grade mineral oil. Examples of suitable, commercially available mineral oils include SONNEBORN™ and CARNATION™ white oils from Witco Corp. (Greenwich, Conn.); ISOPAR™ K and ISOPAR™ H from Exxon Corp. (Houston, Tex.); and DRAKEOL™ and PENETECK™ white mineral oils from Penreco (Karns City, Pa.).

Other preferred non-polar oils are fatty esters having HLB values less than 1.0. These include hydrocarbon plant oils with a high triglyceride content, composed of fatty acid esters and glycerol, whose fatty acids may have varied chain lengths, that can be linear or branched, saturated or unsaturated; these oils are notably wheat germ oil, oils of corn, sunflower, shea butter, castor, sweet almonds, macadamia, apricot, soybean, rapeseed, cotton, alfalfa, poppy, Hokkaido squash, sesame, squash, avocado, hazelnuts, grape or blackcurrent seeds, evening primrose, millet, quinoa, olives, rye, safflower, candlenut tree, passion fruit, Muscat rose; or triglycerides of caprylic/capric acid such as those sold by Stearineries Dubois or those sold under the name MIGLYOL™ 810, 812 and 818 by Dynamit Nobel.

Another exemplary non-polar oil is a synthetic oil or ester with the formula $R^5COOR^6$ in which $R^5$ represents the rest of a higher linear or branched fatty acid with 1 to 40 and better 7 to 19 carbon atoms and $R^6$ represents a branched hydrocarbon chain with 1 to 40 and better 3 to 20 carbon atoms, as for example Purcellin oil (cetostearyl octanoate), isononyl isononanoate, C12 to C15 alcohol benzoate, isopropyl myristate, 2-ethylhexyl palmitate, octanoates, decanoates or ricinoleates of alcohols or polyols; hydroxyl esters such as isostearyl lactate, di-isostearyl malate; and esters of penterythritol; synthetic ethers containing 10 to 40 carbon atoms; and C8 to C26 fatty alcohols such as oleic alcohol; as well as mixtures thereof.

The oil phase in practice typically represents 5 to 99% of the total weight of the composition, preferably 20 to 75%.

The composition of the invention may also include any additive usually used in the field in question, chosen among water (which may be thickened by an aqueous phase thickener or gelling agent), polar liquids such as ethanol, colorants, antioxidants, essential oils, preservatives, aromas, fillers, pasty or waxy lipids, neutralizers, fat soluble polymers, cosmetic or dermatological active ingredients such as emollients, hydrating agents, vitamins, essential fatty adds, sunscreens and their mixtures. Other additives include linear or cyclic silicone oil such as polydimethylsiloxanes (PDMS) which are liquid at room temperature and may or may not be volatile. Polydimethylsiloxanes as used herein preferably contain alkyl, alkoxy or phenyl groups as side chains and/or at silicone chain ends, groups each having 2 to 24 carbon atoms. Other suitable silicon oils include phenylated silicones, such as phenyl trimethicones, phenyl dimethicones and phenyl trimethylsiloxy diphenylsiloxanes, diphenyl dimethicones, diphenyl methyldiphenyl trisiloxanes, and 2-phenylethyl trimethylsiloxy silicates. These additives may be present in the composition at 0 to 20% of the total weight of the composition and better between 0 and 10%.

The additional additives and/or their quantity should be selected such that the advantageous properties of the composition according to the invention, i.e., notably brilliance and non-migration, are not or are not substantially altered by the addition.

The composition according to the invention may be in the form of a dermatological composition for one of care of the skin and/or the hair and nails or in the form of a composition for sun protection, body hygiene, notably a deodorant or makeup remover. In this case it is notably non-colored, possibly containing cosmetic or dermatological active ingredients. In this case it can be used as a care base for the skin, hair and nails or the lips (lip salve protecting the lips from cold and/or sun and/or wind, care cream for the skin the nails or the hair).

The composition of the invention can also be in the form of a colored makeup product for the skin, possibly having care or treatment properties and in particular a foundation, a blush, cheek or eyelid rouge, a product to treat rings under the eyes, an eye liner, a body makeup product; lip makeup such as lipstick possibly having care or treatment properties; makeup for the hair and hard parts such as nails, eyelashes in the form of mascara, eyebrows and hair. In particular, the composition of the invention can be a cosmetic product containing cosmetic and/or dermatological active ingredients.

The composition of the invention must be cosmetically or dermatologically acceptable, i.e., contain a physiologically acceptable and non-toxic medium that can be applied on the skin or lips of the human face. By cosmetically acceptable is meant that the composition has a pleasant appearance, odor and feel.

The coloring material preferably contains primarily pigments and/or mother of pearl in order to obtain a covering makeup, i.e., that masks the skin, lips or nails. Pigments also reduce the sticky feel of compositions, in contrast to soluble colorants.

By "pigment" (mother of pearl (perlescent) or not) is meant any solid particle insoluble in the medium used to impart and/or change a color and/or an iridescent appearance.

Advantageously, the composition contains a coloring matter that may be chosen from among lipophilic colorants, hydrophilic colorants, pigments and perlescent substances usually used in cosmetic or dermatological compositions, and their mixtures. This coloring matter is generally present at 0.01 to 40% of the total weight of the composition, preferably 1 to 35% and better 5 to 25%.

Oil-soluble colorants are, for example, Sudan red, DC Red 17, DC Green 8, beta carotene, soybean oil, Sudan brown, DC Yellow 11, DC Violet 2, DC Orange 5, quinoline yellow. They may represent 0 to 20% of the weight of the composition and better from 0.1 to 6% (if present).

Pigments can be white or colored, inorganic and/or organic, coated or un-coated. Among inorganic pigments, we may mention titanium dioxide, possibly with a surface treatment, zirconium or cerium oxides, as well as the oxides of iron or chromium, manganese violet, ultramarine blue, chromium hydrate and ferric blue. Among organic pigments, we may mention carbon black, D&C pigments and lakes based on cochineal carmine, barium, strontium, calcium, aluminum. Pigments can represent 0 to 40%, preferably 1 to 35% and better 2 to 25% of the total weight of the composition.

Mother of pearl pigments (or pearlescent) can be chosen from among white mother of pearl such as mica coated with titanium or bismuth oxychloride, colored perlescent pigments such as titanium mica with iron oxides, titanium mica with notably ferric blue or chromium oxide, titanium mica with one of the above-mentioned types of organic pigments, as well as bismuth oxychloride. They can represent 0 to 20% of the total weight of the composition and better 0.1 to 15% (if present).

The composition according to the invention can be manufactured by the known processes generally used for cosmetics and skin-care products. It can be manufactured by the process that consists of heating and agitating the ATPA gellant and the non-polar liquid oil to at least the softening temperature of the ATPA, adding the amphiphile compound (s), coloring agent, and additives to it, mixing the whole until a clear, transparent solution is obtained. The homogeneous mixture so obtained, can then be poured into a suitable mold such as a lipstick mold, or directly into the packaging (can or cup, in particular).

Another object of the invention is a cosmetic process for the care, making-up, or treatment of the keratinous substances of human beings, notably the skin, lips, face, and phanera of human beings, comprising the application to the keratinous substances of the composition of the present invention.

Another object of the invention is the use of a sufficient quantity of at least one ATPA gellant molecule of formula (1) and at least one amphiphile compound that is liquid at ambient temperature, or has a melting point of less than 35° C., and having an HLB value of less than 8.0, to structure a liquid oil phase in the form of a self-supporting solid having for example a hardness between 20 and 2,000 g and in particular between 20 and 900 g or better still between 20 and 800 g. This fatty phase is notably that of a cosmetic composition.

Another object of the invention is the use of a sufficient quantity of at least one ATPA gellant molecule of formula (1) and at least one amphiphile compound that is liquid at ambient temperature, or has a melting point of less than 35° C., and has an HLB value of less than 8.0, to structure a liquid oil phase in the form of a self-supporting solid that is glossy and/or non-bleeding.

Another object of the invention is the use of a liquid oil phase structured by at least one ATPA gellant molecule of formula (1) and by an amphiphile compound having an HLB value of less than 8, in a cosmetic composition or for the manufacture of a physiologically acceptable composition that is glossy and/or non-bleeding.

The present invention is applicable not only to makeup products for the lips such as lipstick and lip pencils, but also to products for care and/or treatment of the skin, including the scalp and the lips, such as care creams applied daily, sunscreens for the lips and skin, makeup products for the skin, both the human face and body such as foundations, in particular cast as sticks or cups, products to treat rings under the eyes, and products for non-permanent tattoos (decalcomanias), body hygiene products such as deodorants in particular as sticks, and to eye makeup products such as eye liners, in particular in the form of a pencil or mascaras, notably in the form of a cake.

The invention is illustrated in more detail in the examples that follow. The percentages are given by weight.

EXAMPLES

In the following Examples, softening point was measured using a Model FP83HT Dropping Point Cell from Mettler Instruments, Mettler-Toledo International, Inc. (CH-8606 Greifensee, Switzerland; http://www.mt.com), with a heating rate of 1.5° C./min. Techniques to measure acid and amine numbers are well known in the art and need not be described here. See, e.g., ASTM D-465 (1982) from American Society for Testing and Materials (West Conshohocken, Pa.; http://www.astm.org).

Example 1

Tertiary Amide-terminated Polyamides (ATPA)

Several ATPA's (labeled ATPA A, B, and C) were made from the reactants, and relative amounts thereof, as set forth in Table 1. In Table 1, "DTA" is an abbreviation for di(hydrogenated tallow) amine, "EDA" is an abbreviation for ethylene diamine, "SA" is an abbreviation for stearyl amine, and PD-23™ is a petroleum distillate, all available from Witco Corporation (Greenwich, Conn.; http://www.witco.com). Selected properties for the ATPAs are also set forth in Table 1, including acid number, amine number, softening point ("S.P.") and the appearance when combined at 20 wt % solids in PD-23™ petroleum distillate ("Appearance").

In preparing ATPAs, a 60/40 EDA/DTA equivalent ratio results in a material (ATPA A) that forms a clear, hard gel in PD 23 distillate (at 20% solids). Increasing this ratio to 75/25 (see ATPA B) and 80/20 (see ATPA C) decreases the ATPA's solubility in PD-23™ petroleum distillate, resulting in opaque, hard gels.

TABLE 1

PROPERTIES OF TERTIARY AMIDE-TERMINATED POLYAMIDES

| ATPA | Composition (eq. %) | Acid No. | Amine No. | S.P. (° C.) | Appearance |
|---|---|---|---|---|---|
| A. | 100% EMPOL ™ 1008; 60% EDA, 40% DTA | 20.8 | 25.1 | 82.2 | clear, hard gel |
| B. | 100% EMPOL ™ 1008; 75% EDA, 25% DTA | 11.3 | 10.9 | 101.9 | opaque, hard gel |
| C. | 100% EMPOL ™ 1008; 80% EDA, 20 DTA | 10.3 | 8.0 | 146.9 | opaque, hard gel |

Example 2

Lipstick Formula

| | |
|---|---|
| ATPA A, B, or C (Example 1) | 25.0% |
| Parleam oil | 58.0% |
| Polyglyceryl-2 polyhydroxystearate | 10.0% |
| Pigments (brown iron oxide + titanium oxide) | 9.0% |

Preparation: The ATPA, parleam oil and polyglyceryl-2 polyhydroxy-stearate are heated with mixing to 100° C. until clear and homogeneous, then cooled to 80° C. and the pigments then added. This is all thoroughly mixed using a deflocculating turbine (for example Raynerie), then poured into lipstick moulds.

Example 3

Anhydrous Eye Shadow

| | |
|---|---|
| ATPA A, B, or C (Example 1) | 25.0% |
| Parleam oil | 35.10 |
| Glyceryl oleate | 31.25% |
| Pigments qsp | 100%. |

This eye liner, in stick form, is prepared as in Example 2.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A structured composition comprising at least one liquid oil phase structured by at least one gellant, said at least one gellant comprising a tertiary amide-terminated polyamide resin (ATPA) of the formula (1):

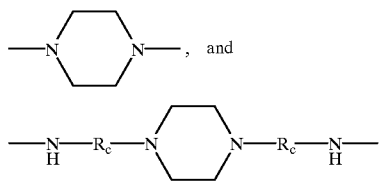

wherein, n designates a number of repeating units such that terminal amide groups constitute from 10% to 50% of the total amide groups;

$R^1$ at each occurrence is independently selected from a $C_{1-22}$ hydrocarbon group;

$R^2$ at each occurrence is independently selected from a $C_{2-42}$ hydrocarbon group;

$R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$;

the composition further comprising at least one amphiphile compound that is a liquid at ambient temperature or has a melting point below 35° C., and has an HLB value of less than 8.0.

2. The composition of claim 1 wherein terminal amide groups of the formula $C(=O)N(R^1)(R^1)$ constitute from 20% to 35% of the total of the amide groups.

3. The composition of claim 1 wherein n is an integer from 1 to 5.

4. The composition of claim 1 wherein $R^2$ is a $C_{30-42}$ hydrocarbon group having the structure of polymerized fatty acid with the carboxylic acid groups removed.

5. The composition of claim 1 wherein between 1% and 50% of the $R^2$ groups are a $C_{4-19}$ hydrocarbon group.

6. The composition of claim 1 wherein $R^3$ is a $C_{2-36}$ hydrocarbon group and $R^{3a}$ is hydrogen.

7. The composition of claim 1 wherein at least 1% of the —N($R^{3a}$)—$R^3$—N($R^{3a}$)— groups are independently selected from polyalkylene amine,

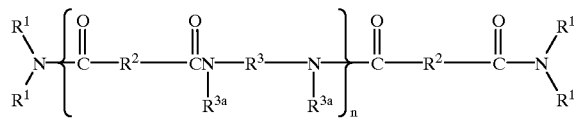

wherein $R^c$ is a $C_{1-3}$alkyl group.

8. The composition of claim 1 further comprising diamide having formula (1) wherein n=0, such that the ratio of terminal amide groups to the total of the amide groups in the resin is from 0.1 to 0.7.

9. The composition of claim 1 in which the amphiphile compound includes a lipophile part bonded to a polar part, with the lipophile part including a carbon chain having at least 8 carbon atoms.

10. The composition of claim 1 in which the amphiphile compound includes a lipophile part bonded to a polar part, with the lipophile part including a carbon chain having at least 16 to 32 carbon atoms.

11. The composition of claim 1 in which the amphiphile compound includes a lipophile part bonded to a polar part, with the lipophile part including a carbon chain having at least 18 to 28 carbon atoms.

12. The composition of claim 9 in which the polar part is selected from the group consisting of alcohols and polyols having from 1 to 12 hydroxyl groups, polyoxyalkylenes having at least 2 oxyalkylene groups and having from 0 to 20 propoxylated groups and/or from 0 to 20 ethoxylated groups.

13. The composition of claim 1 wherein the amphiphile compound is selected from: (a) an ester of stearic, palmitic, behenic, hydroxystearic, oleic, or isostearic acid or mixtures thereof and glycerol, ethylene glycol, propylene glycol, sucrose, sorbitol, or methylglucose; (b) an polyoxyalkene ether of a C-12 to C-26 branched- or linear-chain fatty alcohol or castor oil and; c) a C-12 to C-26 branched-chain fatty alcohol such as octyldodecanol 14. The composition of claim 1 wherein the amphiphile compound is from 2% to 15% of the total weight of the composition.

15. The composition of claim 1 wherein the ATPA is from 5 to 40% of the total weight of the composition.

16. The composition of claim 1 wherein the liquid oil phase comprises more than 50% oil or a mixture of non-polar oils.

17. The composition of claim 1 wherein the liquid oil phase comprises at least one hydrocarbon oil of mineral or synthetic origin.

18. The composition of claim 1 wherein the liquid oil phase comprises at least one oil selected from parleam oil, isoparaffins, and squalane or mixtures thereof.

19. The composition of claim 1 wherein the liquid oil phase is from 5 to 99% of the total weight of the composition.

20. The composition of claim 1 wherein the liquid oil phase is from 20 to 75% of the total weight of the composition.

21. The composition of claim 1 formulated for the care and/or treatment and/or making-up of keratinous substances.

22. The composition of claim 1 further comprising at least one coloring agent.

23. The composition of claim 22 in which the coloring agent is chosen from lipophile coloring agents, hydrophile coloring agents, pigments, mother-of-pearl, and mixtures thereof.

24. The composition of claim 22 in which the coloring agent is from 0.01 to 40% of the total weight of the composition.

25. The composition of claim 1 further comprising at least one additive selected from water, antioxidants, essential oils, preservatives, neutralizers, liposoluble polymers, silicone oil, cosmetic or dermatological active principles, fillers, perfumes, waxes, and mixtures thereof.

26. A structured composition comprising a cosmetically acceptable medium containing at least one liquid-fatty phase structured by at least one gellant, said at least one gellant comprising a tertiary amide-terminated polyamide resin (ATPA) of the formula (1):

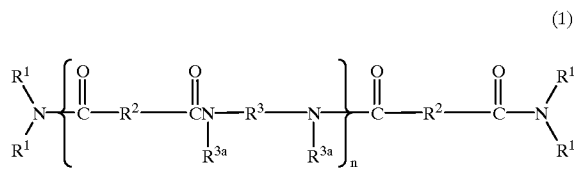

wherein, n designates a number of repeating units such that terminal amide groups constitute from 10% to 50% of the total amide groups;

$R^1$ at each occurrence is independently selected from a $C_{1-22}$ hydrocarbon group;

$R^2$ at each occurrence is independently selected from a $C_{2-42}$ hydrocarbon group;

$R^3$ at each occurrence is independently selected from an organic group containing at least two carbon atoms in addition to hydrogen atoms, and optionally containing one or more oxygen and nitrogen atoms; and $R^{3a}$ at each occurrence is independently selected from hydrogen, $C_{1-10}$ alkyl and a direct bond to $R^3$ or another $R^{3a}$ such that the N atom to which $R^3$ and $R^{3a}$ are both bonded is part of a heterocyclic structure defined in part by $R^{3a}$—N—$R^3$;

the composition further comprising at least one amphiphile compound that is liquid at ambient temperature or has a melting point of less than 35° C., and has an HLB value of less than 8.0.

27. The composition of claim 26 in molded form.

28. The composition of claim 26 in the form of a mascara, eye liner, make-up foundation, lipstick, deodorant, body make-up, make-up remover, eye shadow, rouge, product to remove rings round the eyes, medicated shampoo or creme rinse, insect repellent, sun protection product, or face or body care product.

29. The composition of claim 26 containing pigment.

30. A cosmetic care, make-up or treatment process for the keratinous substances of human beings comprising the application on the keratinous substances of the composition of claim 1.

31. A process for the treatment or care of keratinous substances of a human being, comprising the application on the keratinous substance of the composition of claim 26.

32. A method for forming a structured composition according to claim 1, the method comprising combining ATPA at elevated temperature with at least one liquid oil phase and at least one amphiphile compound that is a liquid at ambient temperature and has an HLB value of less than 8, so as to form a homogenous solution upon stirring, and allowing the homogenous solution to cool to ambient temperature.

33. The method of claim 31 wherein the homogenous solution has a hardness of between 20 and 2,000 g at ambient temperature.

* * * * *

UNITED STATES PATENT AND TRADEMARK OFFICE
CERTIFICATE OF CORRECTION

PATENT NO.     : 6,469,131 B2
DATED          : October 22, 2002
INVENTOR(S)    : Nelson E. Lawson et al.

It is certified that error appears in the above-identified patent and that said Letters Patent is hereby corrected as shown below:

Column 16,
Line 29, "wherein $R^c$" should read as -- wherein $R_c$ --.

Column 18,
Line 43, "The method of claim 31" should read as -- The method of claim 32 --.

Signed and Sealed this

Twenty-second Day of July, 2003

JAMES E. ROGAN
*Director of the United States Patent and Trademark Office*